United States Patent [19]

Thal et al.

[11] Patent Number: 5,189,055
[45] Date of Patent: Feb. 23, 1993

[54] PHENYLPYRROLIC COMPOUNDS USED AS DRUGS, THEIR PREPARATION AND APPLICATION

[75] Inventors: Claude Thal, Sceaux; Olivier Boye, Etiolles; Daniel Guenard, Montrouge; Pierre Potier, Paris, all of France

[73] Assignee: Centre National de la Recherche Scientifique (CNRS), Paris, France

[21] Appl. No.: 655,430

[22] PCT Filed: Sep. 4, 1989

[86] PCT No.: PCT/FR89/00442

§ 371 Date: Apr. 1, 1991

§ 102(e) Date: Apr. 1, 1991

[87] PCT Pub. No.: WO90/02733

PCT Pub. Date: Mar. 22, 1990

[30] Foreign Application Priority Data

Sep. 5, 1988 [FR] France ................................ 88 11592

[51] Int. Cl.$^5$ ................... A61K 31/40; C07D 215/16; C07D 207/30
[52] U.S. Cl. .................................... 514/422; 514/423; 514/312; 546/157; 548/517; 548/532; 548/537
[58] Field of Search ............... 548/517, 532, 537, 517; 546/157; 514/423, 312, 422

[56] References Cited

PUBLICATIONS

CA 112:76858n Novel dimerization . . . pyrroles, Mukherjee et al, 1989, p. 768.
CA 113:115077z Preparation . . . agents, Thal et al., 1990, p. 671.

Primary Examiner—Mary C. Lee
Assistant Examiner—Joseph K. McKane
Attorney, Agent, or Firm—Dressler, Goldsmith, Shore, Sutker & Milnamow, Ltd.

[57] ABSTRACT

The present invention relates to phenylpyrrole compounds, pharmaceutical compositions, preparation and to their application as an active principle, especially as a drug having antimitotic activity.

3 Claims, No Drawings

PHENYLPYRROLIC COMPOUNDS USED AS DRUGS, THEIR PREPARATION AND APPLICATION

The present invention relates to new phenylpyrrole compounds, to their preparation and to their application as an active principle, especially as a drug having antimitotic activity.

The object of the present invention is to propose new compounds which are of use in combating cancer cells, disclosed initially by their reactivity towards tubulin and then by a demonstration of their antimitotic properties.

Tubulin is a cell protein with a molecular weight of the order of 110,000 to 120,000 daltons, consisting of two closely associated subunits, $\alpha$ and $\beta$. It constitutes a basic component whose assembly in helicoid form permits the construction of complex macromolecular structures commonly known as microtubules. The latter are encountered in practically all eukaryotic cells and are used in the formation of many cytoplasmic structures: mitotic spindle, centrioles, flagellae, axonemes, neurotubules, etc. Microtubules thus have fundamental roles, not yet all enumerated, in the life of the cell (division, motility, transport, growth, etc.). The assembling of tubulin is a reversible dynamic mechanism subject to a regulation which has not at present been elucidated.

After extraction of the protein (from pig brain), it is possible to monitor in vitro its assembling and dismantling behaviour under the effect of varying different physicochemical parameters:

- polymerization in the form of microtubules following a temperature rise to 37° C.; promoted by the presence of GTP, polycations, glycerol, etc.
- depolymerization caused by a low temperature (4° C.) and promoted by $Ca^{2+}$ ions, excess GTP, etc.

A number of natural substances are capable of binding to specific tubulin receptor sites. They inhibit its polymerization (colchicine, vinblastine, vincristine, podophyllotoxin, etc.) or its depolymerization (taxol, rhazinilam) and can cause its spiralization (vinblastine).

The present invention has been directed towards substances exhibiting biaryl character, capable of interacting with tubulin and hence exhibiting activity as a mitotic spindle poison. To this end, compounds containing a phenylpyrrole skeleton have been synthesized.

The compounds which are the subject of the present invention correspond to the general formula I

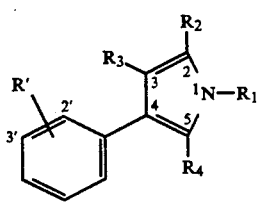

(I)

in which

- $R_1$, $R_2$ and $R_3$, independently of one another, are represented by:
  (1) - H
  (2) - $C_{1-6}$ alkyl,
- R' situated at the 2'- or 3'-position is represented by:

(1) - H
  (2) - $NO_2$

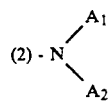

in which $A_1$ and $A_2$, independently of one another, represent:
(a) - H
(b) - $C_{1-4}$ alkyl,
(c) - $C_{1-6}$ alkylene or $C_{1-6}$ alkenylene which cyclizes onto the C atom at the 5-position of the pyrrole ring,

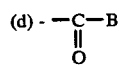

in which B represents:
- phenyl($C_{1-4}$ alkoxy),
- N-benzyloxycarbonylamino ($C_{1-4}$ alkyl),
- $C_{1-6}$ alkylene or $C_{1-6}$ alkenylene which cyclizes onto the C atom at the 5-position of the pyrrole ring.
- $R_4$ is represented by:
  (1) - 5- or 6-membered heterocycloalkyl($C_{1-4}$ alkyl),

in which Y represents:
(a) - $C_{1-4}$ alkoxy
(b) - N,N'-(5- to 6-membered cycloalkyl)-(ureido)
(c) - amino cyclizable at the R'-position.

The present invention also relates to the preparation of the compounds represented by the general formula I. This preparation process is characterized in that a nitrostyrene of formula II is reacted. [sic]

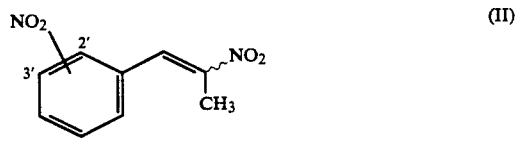

in which:
the $NO_2$ group is situated at the 2'- or 3'-position, with an alkyl isocyanoacetate of formula III

in which:
R is an ethyl or methyl group.

The reaction is carried out according to the method of Barton and Zard permitting the formation of pyrroles from aliphatic or aromatic nitroalkenes, in a THF/absolute tert-butanol (2:1) mixture at a temperature of 40°-50° C. The starting point of the reaction is the Michael type addition of an α-isocyanoacetate to the nitrostyrene in the presence of a base, in this case DBU.

The nitrostyrene used is prepared beforehand by the condensation of nitroethane with the corresponding nitrobenzaldehyde according to a Knoevenagel reaction.

From the nitrostyrenes, access is hence gained directly or via a simple functional conversion to the phenylpyrroles which are the subject of the present invention.

Thus, in the case where the compound I' is obtained

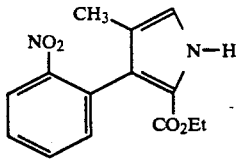

(I')

it is converted to other compounds represented by the general formula I according to one or more of the following conversions:

(1) - simultaneous reduction of the nitro group of the aromatic ring and the ester function of the pyrrole ring, and in this case cyclization, (2) - reduction of the nitro group to amine, (3) - acylation of the amine function obtained according to (2), (4) alkylation of the carbamate obtained according to (3), optionally followed by a hydrogenolysis, (5) - saponification of the ester function of the pyrrole ring, (6) - condensation of N,N'-cyclohexylurea [sic] with the acid function obtained according to (5), (7) - reduction of the acid function obtained according to (5) to aldehyde, (8) - Horner-Emmons condensation on the aldehyde function obtained according to (6), (9) - electrophilic substitution on the pyrrole ring,

(10) intramolecular cyclization reaction between the two aromatic rings.

The creation of a third ring according to the latter conversion, joining the aromatic rings, is carried out using chains bearing functional groups, or using reactive groups attached, where appropriate using one or more of the conversions mentioned above, to each of the rings, phenyl and pyrrole, which permit an intramolecular type closing.

In the light of their advantageous antimitotic properties, the phenylpyrrole compounds represented by the general formula I prove useful as drugs. The invention also encompasses pharmaceutical compositions, characterised in that they contain as active principle a compound of general formula I.

Other features and advantages of the present invention will become apparent on reading the description given below, in particular with the aid of a number of examples given simply by way of illustration.

The phenylpyrrole compounds which follow were prepared according to the procedure described below in II, from the corresponding nitrostyrenes, themselves synthesized beforehand according to method I.

I Preparation of nitrostyrenes

The aldehyde (2 mmol) is dissolved in the buffer mixture: 10 ml glacial acetic acid/600 mg ammonium acetate. 1.4 equivalents of nitroethane are added and the mixture is brought to reflux. After 3 to 4 hours, the aldehyde has disappeared and a less polar main product is formed. The reaction mixture is poured into 20 ml of ice-cold water and the resulting mixture is extracted with methylene chloride. The organic phase is washed twice with water and twice with carbonated water, then dried over sodium sulfate and finally evaporated.

The nitrostyrene is isolated on a silica column (eluent: $CH_2Cl_2$/hexane, 4:1).

II General method of preparation of phenyloyrrole type compounds from the corresponding nitrostyrenes The nitrostyrene (20 mmol) is dissolved in 50 ml of a distilled tetrahydrofuran/absolute tert-butanol (2:1) mixture. 1.5 equivalents of DBU are added, followed, dropwise and at room temperature, by 1.2 equivalents (2.7 ml) of ethyl isocyanoacetate. The reaction mixture is brought to 40°-50° C. and stirred for 3 to 4 hours (except where otherwise stated). Reaction is complete and a less polar major product than the starting nitrostyrene forms. The phenylpyrroles thereby obtained are visualized in pink on a chromatographic plate on spraying with vanillin/concentrated HCl mixture. The solvents are evaporated off and the product is separated directly on a silica column (eluent:$CH_2Cl_2$/hexane, 4:1).

Note: Replacement of ethyl isocyanoacetate by methyl isocyanoacetate gives the methyl ester in the same yield.

EXAMPLE 1

Ethyl 4-methyl-3-phenyl-2-pyrrolecarboxylate

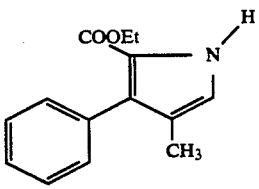

(1)

The synthesis is carried out starting with 1-phenyl-2-nitro-1-propene according to general method II. The ethyl 4-methyl-3-phenyl-2-pyrrolecarboxylate thereby obtained is purified on a silica column to give a white powder (3.9 g ; Yld=85%).

. M.p.:62°-64° C.

. IR ($CHCl_3$):3480, 3300, 2990, 2940, 1675, 1490, 1460, 1290 $cm^{-1}$

. UV (methanol): λmax: 276.4 220.3 207.2 nm ε: 13900 11700 12800 $mole^{-1} \times 1 \times cm^{-1}$ . MS:m/z:229 (M+·), 200, 183, 156, 155, 154

Microanalysis $C_{14}H_{15}NO_2$ calculated %:C 73.34 H 6.59 N 6.10 found %:72.85 6.38 6.06

| $^1H$ NMR (CDCl$_3$, 400 MHz) | |
|---|---|
| 1.1 | (3H, t J=7Hz, CH$_2$C$\underline{H}_3$) |
| 2 | (3H, s, CH$_3$) |
| 4.05 | (2H, q J=7Hz, C$\underline{H}_2$CH$_3$) |
| 6.7 | (1H, d, pyrrole H) |
| 7.15-7.4 | (5H, m, Ph) |
| 9.15 | (1H, br, NH) |

EXAMPLE 2

Methyl 4-methyl-3-(3'-nitrophenyl)-2-pyrrolecarboxylate

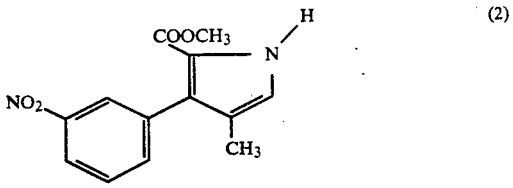
(2)

This is obtained from 1-(3,-nitrophenyl)-2-nitro-1-propene according to procedure II. 4.2 g of compound (2) are obtained (Yld: 80%), which compound may be recrystallized in an ethyl acetate/hexane mixture.
. M.p.:146° C.
. IR (CHCl$_3$):3460, 1690 (COOMe), 1540, 1360, 1160 cm$^{-1}$
. UV (absolute ethanol) λmax:270.2 205.5 nm ε:16700 13700 mole×1$^{-1}$×cm$^{-1}$ [sic]
. MS:m/z:260 (M+·), 228, 153
. Microanalysis C$_{13}$H$_{12}$N$_2$O$_4$
calculated %:C 59.99 H 4.65 N 10.77 O 24.59
found %:60.07 4.84 10.82 24.82

| $^1$H NMR (CDCl$_3$, 200 MHz) | |
|---|---|
| 2.03 | (3H, s, OCH$_3$) |
| 3.75 | (3H, s, CH$_3$) |
| 6.91 | (1H, d J=2Hz, pyrrole H) |
| 7.63 | (1H, t J=8Hz, H$_5$') |
| 7.8 | (1H, d J=8Hz, H$_6$') |
| 8.28 | (1H, d J=8Hz, H$_4$') |
| 8.33 | (1H, s, H$_2$') |
| 9.33 | (1H, br, NH) |

EXAMPLE 3

3-Methylpyrrolo[2,3-c]quinolin-4(5H)-one

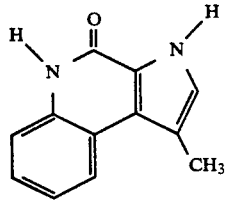
(4)

The synthesis is carried out in several steps, starting with 1-(2'-nitrophenyl)-2-nitro-1-propene prepared beforehand according to method I:

a) Synthesis of ethyl 4-methyl-3-(2'-nitrophenyl)-2-pyrrolecarboxylate (3)

This is carried out starting with 1-(2'-nitrophenyl)-2-propene according to the procedure described in II.

Purification on a silica column gives 5.4 g of a yellow powder (Yld=98%). Recrystallization of the product in a DMSO/H$_2$O mixture enables yellow crystals to be obtained (m.p. 116° C.).

b) Synthesis of 3-methylpyrrolo[2,3-c]quinolin-4(5H)-one:(4)

The following are mixed in 10 ml of methanol: 274 mg (1 mmol) of (3), 1 g of FeCl$_3$.6H$_2$O (and 50 mg of activated charcoal). The reaction mixture is brought to reflux for 10 minutes and 1.5 equivalents of hydrazine are then added dropwise. Reflux is maintained for 12 hours. The expected product (4) appears, as well as ethyl 3-(2'-aminophenyl)-4-methylpyrrolecarboxylate, compound (5).

The catalyst is filtered off on celite and the solution collected is allowed to cool, in which solution the cyclization product crystallizes. 80 mg of off-white cyrstals are collected (Yld=40%). The solution containing the reduction product is evaporated and the latter is purified by chromatography on a silica column (110 mg of (5) are obtained, Yld=45%).
. Analyses of (4)
. M.p.:254°–256° C.
. IR (nujol):1620 cm$^{-1}$
. UV (DMSO):λmax: 320 306 258 nm ε:11100 9700 8200 mole$^{-1}$×1×cm$^{-1}$
. MS:m/z:198 (M+·), 197, 179, 169

| $^1$H NMR (CD$_3$OD, 60 MHz) | |
|---|---|
| 2.5 | (3H, s, CH$_3$) |
| 7.1–7.5 | (5H, m, Ph, pyrrole H) |
| 8.1 | (1H, m, CONH) |

. Analyses of (5)
. MS:m/z:224 (M+·), 199 (M-OEt)

| $^1$H NMR (CDCl$_3$, 60 MHz) | |
|---|---|
| 1.06 | (3H, t J=7Hz, CH$_2$CH$_3$) |
| 1.91 | (3H, s, CH$_3$) |
| 3.38 | (2H, br, NH$_2$) |
| 4.13 | (2H, q J=7Hz, CH$_2$CH$_3$) |
| 6.53–7.33 | (5H, m, Ph, pyrrole H) |

EXAMPLE 4

Ethyl 3-[2'-(N-benzyloxycarbonylglycylamido)phenyl]-4-methyl-2-pyrrolecarboxylate

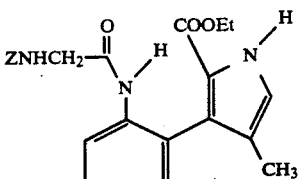
(6)

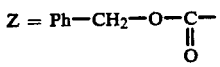

The synthesis of the compound (6) is carried out starting with ethyl 3-(2'-aminophenyl)-4-methyl-2-pyrrolecarboxylate (5) obtained in Example 3.

843 mg (4.05 mmol) of glycine N-benzylcarbamate [sic] (Z-glycine) are dissolved in 80 ml of anhydrous tetrahydrofuran. 580 mg (4.05 mmol) of N-methylmorpholine are added to the solution placed under argon and cooled to −15° C., followed by the dropwise addition of 570 mg of isobutyl chloroformate. After 10 minutes' stirring at −15° C., a solution of 500 mg (2.23 mmol) of (5) in 50 ml of tetrahydrofuran is introduced dropwise. The temperature of the reaction medium is maintained for 5 minutes at −15° C.; the mixture is then returned to room temperature. Reaction is complete in 1 hour.

The N-methylmorpholine salt is filtered off and washed with tetrahydrofuran. After evaporation of the tetrahydrofuran, the residue is taken up with ethyl acetate; the insoluble portion is filtered off; the organic phase is washed successively with acidulated water (0.1N HCl) and water saturated with sodium carbonate and then with sodium chloride. After drying over sodium sulfate and evaporation, 700 mg of ethyl 3-[4',5'-dimethoxy-2'-(N-benzyloxycarbonylglycylamido)-phenyl]-4-methylpyrrolecarboxylate [sic] are isolated (Yld=79%). Recrystallization in an ethyl acetate/hexane mixture gives pale yellow crystals.

. M.p.:124° C.
. IR (CHCl$_3$):3460, 1690, 1590, 1510, 1290 cm$^{-1}$
. UV (DMSO):λmax: 258 nm ε:11300 mole$^{-1}$×1×cm$^{-1}$
(absolute ethanol) λmax:276 (shoulder), 239, 207 nm
. MS:m/z:435 (M+·), 244, 243, 199
. Microanalysis:C$_{24}$H$_{25}$N$_3$O$_5$
calculated %:C 66.19 H 5.78 N 9.65 O 18.37
found %:65.97 5.63 9.68 18.65

| $^1$H NMR (CDCl$_3$, 80 MHz) | |
|---|---|
| 0.95 | (3H, t J=7Hz, CH$_2$C$\underline{H}_3$) |
| 1.8 | (3H, s, CH$_3$) |
| 3.72 | (2H, d, J=5Hz, CH$_2$NH) |
| 4 | (2H, q J=7Hz, C$\underline{H}_2$CH$_3$) |
| 5 | (2H, s, C$\underline{H}_2$ Ph) |
| 5.66 | (1H, br, CH$_2$N$\underline{H}$) |
| 6.61 | (1H, d, J=2Hz, pyrrole H) |
| 7–7.25 | (8H, m, Ph) |
| 7.87 | (1H, br, s, Ph N$\underline{H}$) |
| 8.2 | (1H, d, J=7Hz, H$_3$') |

EXAMPLE 5

1,4-Dimethyl-3-(2'-nitrophenyl)pyrrole-2(N,N'-cyclohexylureidocarboxamide) [sic]

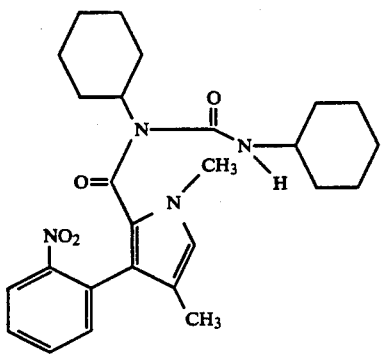

(10)

This is synthesized from ethyl 4-methyl-3-(2'-nitrophenyl)2-pyrrolecarboxylate (3) prepared according to the procedure described above in Example 3.

a) Synthesis of ethyl 1,4-dimethyl-3-(2'-nitrophenyl)-2-pyrrolecarboxylate (7)

1 g (3.65 mmol) of (3) is dissolved in 20 ml of anhydrous tetrahydrofuran. The mixture is cooled in ice and the anion is formed by adding one equivalent of sodium hydride. After 15 minutes' stirring while the mixture is cold, the latter is raised to room temperature. 1.3 equivalents of methyl para-toluenesulfonate are then added and the reaction mixture is heated to 50° C. for 3 hours. The reaction is quantitative. A less polar product than (3) is formed. The mixture is allowed to cool and is filtered on celite, and the latter is washed with methylene chloride. The product is obtained in the form of a yellow oil after purification on a silica column (eluent:CH$_2$Cl$_2$/hexane, 3:2). 0.95 g of (7) is obtained (Yld:90%).

b) Synthesis of 1,4-dimethyl-3-(2-nitrophenyl)-2-pyrrolecarboxylic acid (8)

(7) is saponified in a methanol/30% sodium hydroxide (5:1) mixture in the heated state (60° C.) for 2 hours. The solution is acidified to pH 3 while cooling in ice. The acid precipitates and is extracted with methylene chloride. The organic phase is washed with water saturated with sodium chloride and dried over sodium sulfate. The product is purified on a silica column (eluent:CH$_2$Cl$_2$/MeOH 95:5). The expected compound (8) is isolated in the form of yellow crystals, which are recrystallized in an ethyl ether/hexane mixture, m.p. 205° C.(190 mg; Yld : 73%).

c) Synthesis of 1,4-dimethyl-3-(2'-nitrophenyl)pyrrole-2-(N,N'-cyclohexylureidocarboxamide) [sic] (10)

78 mg (1.5 equivalents) of glycine ethyl ester hydrochloride and 0.08 ml (1.5 equivalents) of anhydrous triethylamine are dissolved in 5 ml of acetonitrile. 100 mg (0.38 mmol) of (8) are added and the solution is cooled to −5° C.

117 mg of dicyclohexylcarbodiimide (DCCI) are then introduced; the reaction mixture is stirred for 4 hours at −5° C. and then 12 hours at room temperature. On a chromatographic plate, 2 products less polar than the acid (8) are seen to appear. They are the expected compound (10) and 1,4-dimethyl-3-(2'-nitrophenyl)pyrrole-2-(glycylcarboxamide ethylate) [sic] (11).

The acid is not completely consumed. The reaction solvent is evaporated off and the residue is taken up with ethyl acetate. The insoluble portion is filtered off; the organic phase is washed successively with water saturated with sodium carbonate, 1N hydrochloric acid solution and water saturated with sodium chloride. After drying over sodium sulfate and evaporation, 160 mg of a crude mixture of 2 products are obtained, which products are separated on a silica column; this giving: (10):70 mg (Yld=39%)
. MS:m/z:466 (M+·), 341, 243, 199

| $^1$H NMR (CDCl$_3$, 80 MHz) | |
|---|---|
| 1–1.87 | (22H, br, cyclohexyl H) |
| 1.8 | (3H, s, CH$_3$) |
| 3.6 | (3H, s, N CH$_3$) |
| 6.47 | (1H, s, pyrrole H) |
| 7.2–7.7 | (3H, m, Ph) |

| ¹H NMR (CDCl₃, 80 MHz) | |
|---|---|
| 7.87 | (1H, d J=7Hz, H₃,) |

EXAMPLE 6

5-Butyl-1,4-dimethyl-2-(1,4-dioxa-2-ethylcarbaldehyde)-3-[2'-(N-benzyloxycarbonyl-N-methylamino)-phenyl]pyrrole [sic]

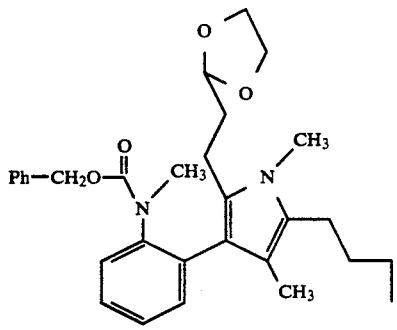

(22)

This is obtained from ethyl 1,4-dimethyl-3-(2'-nitrophenyl)-2-pyrrolecarboxylate (7), the preparation of which has been described in Example 5. The synthesis of the compound (22) necessitates the following steps:

a) Synthesis of 1,4-dimethyl-2-hydroxymethyl-(2'-nitrophenyl) pyrrole (12)

200 mg (7) are dissolved in 30 ml of anhydrous methylene chloride and the solution is cooled to −78° C. in a bath (acetone/dry ice). 2.8 ml (4 equivalents) of 1M dibal in toluene are added dropwise. Stirring is maintained for 2 hours at −78° C., the flask is then removed from the cooling medium and 50 ml of aqueous (10%) sodium carbonate solution are introduced. A substantial emulsion appears, and is removed by filtration on celite. The clear organic phase collected is washed with water saturated with sodium chloride and dried over sodium sulfate. The alcohol (12) is purified on a silica column (120 mg ; Yld 71%).

b) Synthesis of 1,4-dimethyl-3-(2'-nitrophenyl)pyrrole-carbaldehyde (13)

100 mg of MnO₂, prepared according to Attenburrow's method, are suspended in a carbon tetrachloride/methylene chloride (4:1) mixture containing 500 mg of alcohol (12). The reaction medium is stirred at room temperature for 1½ hours. The oxidizing agent is then filtered on celite. 230 mg of compound (13) are obtained (Yld:46%). This compound is purified by chromatography on a silica column (eluent:ethyl acetate/hexane, 1:1). It has the appearance of a yellow oil.

c) Synthesis of 1,4-dimethyl-3-(2'-nitrophenyl)-2-(2-carboxyvinyl ethylate)pyrrole [sic] (14)

470 mg (3 equivalents) of sodium hydride (powder, 97% pure) are suspended under argon in 40 ml of anhydrous ethylene glycol dimethyl (DME). The mixture is cooled in ice and 3.9 ml (3 equivalents) of triethylphosphonoacetate diluted in 5 ml of DME are added. Gaseous evolution takes place and the reaction mixture is stirred at room temperature until the hydride has been completely consumed. Into the reaction solution, which has become clear, 1.6 g of (13) dissolved in 30 ml of DME are introduced.

After 6 hours' stirring at room temperature, the reaction mixture is filtered on celite. The DME is evaporated off and the residue is taken up with methylene chloride. The organic phase is washed with aqueous sodium chloride solution until the emulsion produced has disappeared, and then dried over sodium sulfate. After evaporation of the solvent, 4 g of crude product are obtained, which product, when purified on a silica column (eluent:ethyl acetate/hexane, 2:3), yields a yellow powder of compound (14) (2 g:Yld 97%).

d) Synthesis of 5-(1-butenyl)-1,4-dimethyl-2-(2-carboxyvinyl ethylate)-3-(2'-nitrophenyl)pyrrole [sic]:(15)

4 g (12.7 mmol) of (14) are dissolved at 0° C. in 60 ml of a tetrahydrofuran/6% HCl mixture (50 ml of tetrahydrofuran/10 ml of 36% hydrochloric acid). 1.5 ml (3 equivalents) of butyraldehyde are added dropwise. The reaction mixture is stirred for 7 hours in the cold. The acid solution is neutralized with saturated aqueous sodium carbonate solution and the product is then extracted with ethyl acetate. The organic phase is washed with carbonated water (10%) and then dried over sodium sulfate. The compound (15) obtained is purified on a silica column (eluent:ethyl acetate/hexane, 1:4). Red crystals are obtained (1.8 g; Yld: 38%).

e) Synthesis of 5-(1-butenyl)-1,4-dimethyl-2-(2-hydroxymethylvinyl)-3-(2'-nitrophenyl) pyrrole:(16)

4 g of the compound (15) are reduced with 3 equivalents of diisobutylaluminum hydride. The compound (16) is isolated in the form of a red powder (3 g; Yld=85%).

f) Synthesis of 5-(1-butenyl)-1,4-dimethyl-3-(2'-nitrophenyl)-2-(2-vinylcarbaldehyde) pyrrole [sic]:(17)

3 g of (16) are oxidized in the course of 1½ hours with 20 g of manganese dioxide, prepared according to Attenburrow's method, in 60 ml of carbon tetrachloride. After filtration of the reaction mixture on celite and purification of the product on a silica column, orange-red crystals of compound (17) are isolated (2 g; Yld=67%).

g) Synthesis of 5-(1-butenyl)-1,4-dimethyl-3-(2'-nitrophenyl)-2-(1,4-dioxa-2-vinylcarbaldehyde)-pyrrole [sic]:(18)

2.6 g (8 mmol) of (17) and 4.5 ml (10 equivalents) of ethylene glycol as well as a catalytic amount (20 mg) of pyridinium tosylate are dissolved in 60 ml of benzene. The reaction mixture is brought to reflux for 4 hours and turned green. (The water is removed azeotropically using a Dean and Stark apparatus). A less polar product than the aldehyde is formed. After cooling, the benzene phase is washed 3 times with aqueous sodium carbonate solution and dried over sodium sulfate. The crude product obtained after evaporation is purified on an alumina column (eluent:ethyl acetate/hexane, 2:3); it has the appearance of a red paste (we noted a slight instability of the product during its passage through silica). 2.2 g of compound (18) are obtained (Yld=75%).

h) Synthesis of 3-(2'-aminophenyl)-5-(1-butenyl)-1,4-dimethyl-2-(1,4-dioxa-2-vinylcarbaldehyde)pyrrole [sic]:(19)

The compound (18) is reduced with hydrazine in ethanol in the presence of Raney nickel. 2 g of compound (18) give 1.7 g of a yellow paste of compound (19) (Yld =93%).

i) Synthesis of 3-(2'-aminophenyl)-5-butyl-1,4-dimethyl-2-(1,4-dioxa-2-ethylcarbaldehyde)pyrrole [sic]:(20)

1.9 g of (19) is reduced in 40 ml of ethanol in the presence of 400 mg of palladium on charcoal (10%) under a hydrogen atmosphere. After 12 hours' reaction, the catalyst is filtered off on celite and the product is purified on an alumina column (eluent:ethyl acetate/hexane, 2:3). The compound (20) is isolated in the form of a yellow paste (1.6 g; Yld=83%).

j) Synthesis of 3-(2'-benzyloxycarbonylaminophenyl)-5-butyl-1,4-dimethyl-2-(1,4-dioxa-2-ethylcarbaldehyde) pyrrole [sic]:(21)

1.6 g of (20) are dissolved in 150 ml of anhydrous ethylene glycol dimethyl ether (DME). The solution is cooled in ice and 5.5 ml (20 equivalents) of distilled pyridine are added. A solution of 1.2 ml (1.8 equivalents) of benzyl chloroformate in 20 ml of DME is then introduced dropwise in the course of two hours (slow introduction of the reagent gives a better yield). The reaction medium is stirred for one hour at room temperature and the pyridinium hydrochloride formed is then filtered off. The DME is evaporated off and the residue is taken up with ethyl acetate; the organic phase is washed with saturated aqueous solutions of sodium chloride and sodium carbonate, then dried over sodium sulfate and evaporated. The compound (21) is obtained in the form of a yellow oil, which is purified on an alumina column (eluent:ethyl acetate/hexane, 2:3) (Yld=67%).

k) Synthesis of 5-butyl-1,4-dimethyl-2-(1,4-dioxa-2-ethylcarbaldehyde)-3-[2'-(N-benzyloxycarbonyl-N-methylamino)phenyl]-pyrrole [sic]:(22)

1.5 g of (211 is dissolved under argon in 100 ml of anhydrous DME. After the mixture has been cooled to −20° C. (ice/sodium chloride), the anion of (21) is formed by adding 453 mg (1.3 equivalents) of potassium tertbutylate. The yellow solution turns red-brown and a precipitate appears. The reaction mixture is stirred for 30 minutes at −20° C. and 0.6 ml (3 equivalents) of methyl iodide is then introduced dropwise. Stirring is continued for one hour at −20° C. The precipitate is removed by filtration on celite; the DME is evaporated off and the residue is taken up with ethyl acetate. After being washed with a saline solution of sodium chloride [sic], the organic phase is dried over sodium sulfate and evaporated. The product is purified on an alumina column (eluent:ethyl acetate/hexane, 2:3). A yellow oil is isolated. The compound (22) thereby obtained is a mixture of diastereoisomers (1.1 g; Yld=71%).

. IR (C6H6):2980, 2940, 2880, 1710, 1450, 1390, 1350, 1160 cm−1.
. UV (DMSO):λmax:208 nm
(absolute ethanol):max: 208 nm . MS:m/z:490 (M+·), 447 (M-CH2CH2CH3), 403, 390, 220, 205

| 1H NMR (C6D6, 200 MHz) | |
| --- | --- |
| 0.87 | (3H, t J=7Hz, CH2CH3) |
| 1.29 | (4H, m, CH2CH2CH3) |
| 1.91 | (5H, br, s, CH2CHOO, CH3) |
| 2.41 | (2H, br, t, CH2CH2CH2) |
| 2.78 | (2H, m, CH2CH2CHOO) |
| 3.03 | (3H, s, NCH3) |
| 3.09 | (3H, s, NCH3) |
| 3.41 | (4H, m, OCH2CH2O) |
| 4.65 | (1H, t, CHOO) |
| 5.3 | (2H, br s, Ph CH2) |
| 6.85–7.9 | (4H, m, Ph) |

EXAMPLE 7

5-Butyl-1,4-dimethyl-2-(1,4-dioxa-2-ethylcarbaldehyde)-3-[2'-(N-methylamino)phenyl]pyrrole [sic]

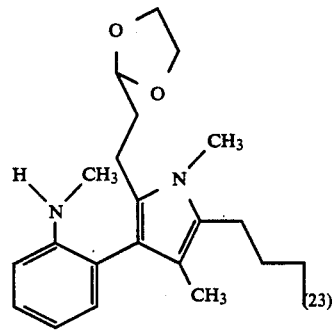

This compound is obtained by hydrogenolysis of the benzyl carbamate group of the compound (22). The hydrogenolysis is carried out under a hydrogen atmosphere, in the presence of palladium on charcoal (10% Pd) in ethyl acetate. After 15 hours' stirring, the catalyst is filtered off on celite and the product is then purified on an alumina column (eluent:ethyl acetate/hexane, 3:7). 1 g of compound (22)yields, after deprotection, 500 mg of a red-brown oily product (23) (Yld=70%).

. IR (C6H6):3350 (broad signal), 2900, 2850, 1680, 1600, 1360, 1120 cm−1.
. UV (DMSO):[lacuna] max:306 (shoulder) 257 nm
. MS:m/z:356 (M+·), 269

| 1H NMR (C6D6, 200 MHz) | |
| --- | --- |
| 0.87 | (3H, t J=7Hz, CH2CH3) |
| 1.33 | (4H, m, CH2CH2CH3) |
| 1.95 | (2H, m, CH2CHOO) |
| 2.03 | (3H, s, CH3) |
| 2.45 | (3H, d J=5Hz, CH3NH) |
| 2.47 | (2H, t J=7Hz, CH2CH2CH2CH3) |
| 2.78 | (2H, m, CH2CH2CHOO) |

-continued

¹H NMR (C₆D₆, 200 MHz)

| 3.16 | (3H, s, NCH₃) |
| 3.39 | (4H, m, OCH₂CH₂O) |
| 4.03 | (1H, q J=5Hz, CH₃NH) |
| 4.64 | (1H, t J=5Hz, CH₂CHOO) |
| 6.74 | (1H, d J=8Hz, H₆') |
| 6.95 | (1H, t J=8Hz, H₄') |
| 7.36 | (2H, m, H₃', H₅') |

Biological study

The evaluation of the biological activity of the products synthesized was performed employing several biological tests: after the interaction of these compounds with tubulin (inhibition of polymerization or of depolymerization) had been studied, and their activity as a mitotic spindle poison had been demonstrated in this manner, cytotoxicity studies were undertaken.

The cytotoxicity studies were carried out, on the one hand on the Vero line (normal monkey kidney cell), Table I, and on the other hand on the KB line (human carcinoma of the nasopharynx), Table II, according to the following method:

Materials and method

The products were introduced at the time of culturing, which is maintained for 72 hours. The products are tested at 100, 80, 40, 20 and 10 μm [sic]. At these concentrations, the DMSO used for dissolving the compounds does not exceed 1% in the cultures and is non-toxic. The percentage values for inhibition of cell proliferation were measured by a colorimetric method with crystal violet, relative to control cultures containing DMSO (≦1%).

TABLE I

| Vero cells Concentration in μm [sic] | Products subjected to the cytostasis tests % inhibition of proliferation Compound No. | | | | | | |
|---|---|---|---|---|---|---|---|
| | (1) | (2) | (4) | (6) | (10) | (22) | (23) |
| 100 | 63 | 77 | 69–84 | 78 | 100 | 54 | 80 |
| 80 | 46 | 75 | 49–70 | 48 | 100 | 54 | 69 |
| 40 | 20 | 38 | 45 | 4 | 25 | 0 | 25 |
| 20 | 0 | 3 | 0 | 0 | 0 | 0 | 0 |
| 10 | 0 | 0 | 0 | 0 | 0 | 0 | 0 |

TABLE II

| KB cells Concentration in μm [sic] | Products subjected to the cytostasis tests % inhibition of proliferation Compound No. | | | | | | |
|---|---|---|---|---|---|---|---|
| | (1) | (2) | (4) | (6) | (10) | (22) | (23) |
| 100 | 43 | 72 | 68 | 68 | 45 | 59 | 100 |
| 80 | 35 | 50 | 60 | 52 | 27 | 44 | 94 |
| 40 | 0 | 10 | 100 | 31 | 0 | 0 | 81 |
| 20 | 0 | 0 | 72 | 22 | 0 | 0 | 66 |
| 10 | 0 | 0 | 0 | 0 | 0 | 0 | 48 |
| 5 | x | x | x | x | x | x | 4 |

Results

The compounds of the present invention, especially those of Examples 4, 6 and above all 23, prove especially advantageous. They show some degree of selectivity at low concentration with respect to the KB line.

The present invention also relates to pharmaceutical compositions containing as active principles at least one compound represented by the general formula I, in combination with any conventional pharmacological vehicle enabling it to be administered, especially orally and parenterally.

We claim:

1. A compound selected from the class consisting of:
   - ethyl 4-methyl-3-phenyl-2-pyrrolecarboxylate,
   - methyl 4-methyl-3-(3'-nitrophenyl)2-pyrrolecarboxylate,
   - 3-methylpyrrolo[2,3-c]quinolin-4(5H)-one,
   - ethyl 3-[2'-(N-benzyloxycarbonylglycylamido)-phenyl]-4-methyl-2-pyrrolecarboxylate,
   - 1,4-dimethyl-3-(2'-nitrophenyl)pyrrole-2-(N,N'-cyclohexylureidocarboxamide),
   - 5-butyl-1,4-dimethyl-2-(1,4-dioxa-2-ethylcarbaldehyde)-3-[2'-(N-benzyloxycarbonyl-N-methylamino)-phenyl]pyrrole,
   - 5-butyl-1,4-dimethyl-2-(1,4-dioxa-2-ethylcarbaldehyde)-3-[2'-(N-methylamino)phenyl]pyrrole.

2. Pharmaceutical compositions, characterized in that they contain as active principle at least one compound of general formula I according to claim 1.

3. The method of combating cancer cells in a patient which comprises administering to said patient a tubulin-interacting amount of a compound in accordance with claim 1.

* * * * *